United States Patent
Tacchini et al.

(10) Patent No.: US 12,121,927 B2
(45) Date of Patent: Oct. 22, 2024

(54) APPARATUS AND METHOD FOR COATING AN INJECTION MEDICAL DEVICE

(71) Applicant: NUOVA OMPI S.R.L. Unipersonale, Piombino Dese (IT)

(72) Inventors: Paolo Tacchini, Zola Predosa (IT); Filippo Tonini, Bologna (IT); Fabio Chinellato, Treviso (IT); Alberto Chillon, San Vito di Vigonza (IT)

(73) Assignee: NUOVA OMPI S.R.L. UNIPERSONALE, Piombino Dese (IT)

( * ) Notice: Subject to any disclaimer, the term of this patent is extended or adjusted under 35 U.S.C. 154(b) by 0 days.

(21) Appl. No.: 18/447,468

(22) Filed: Aug. 10, 2023

(65) Prior Publication Data
US 2024/0050979 A1   Feb. 15, 2024

(30) Foreign Application Priority Data

Aug. 11, 2022 (IT) .......... 102022000017178

(51) Int. Cl.
| | |
|---|---|
| *B05C 11/10* | (2006.01) |
| *B05C 5/02* | (2006.01) |
| *B05B 1/24* | (2006.01) |
| *B05B 9/00* | (2006.01) |

(52) U.S. Cl.
CPC .......... *B05C 11/1042* (2013.01); *B05C 5/02* (2013.01); *B05B 1/24* (2013.01); *B05B 9/002* (2013.01)

(58) Field of Classification Search
None
See application file for complete search history.

(56) References Cited

U.S. PATENT DOCUMENTS

| | | | | |
|---|---|---|---|---|
| 6,534,112 | B1* | 3/2003 | Bouchier | A61L 29/16 427/430.1 |
| 7,231,716 | B2* | 6/2007 | Verilli | B21J 5/10 29/890.132 |
| 7,597,764 | B2* | 10/2009 | Verlee | A61P 7/02 118/667 |
| 8,210,455 | B2* | 7/2012 | Newbold | B21J 5/10 29/890.142 |
| 8,640,643 | B2* | 2/2014 | Wenc | A61L 31/10 118/503 |

(Continued)

FOREIGN PATENT DOCUMENTS

CN          215688652 U    2/2022

OTHER PUBLICATIONS

Search Report issued in corresponding IT Application No. 102022000017178 dated Mar. 3, 2023.

*Primary Examiner* — Jethro M. Pence

(57) ABSTRACT

An apparatus for coating an injection medical device includes an inlet tank fillable with a coating substance, a delivery nozzle configured to deliver the coating substance to an injection medical device, and a supply assembly interposed between, and in fluid communication with, the inlet tank and the delivery nozzle, the supply assembly being configured to withdraw the coating substance from the inlet tank and to supply it to the delivery nozzle. The supply assembly includes at least one sterilisation filter configured to filter the coating substance withdrawn from the inlet tank. A method of for coating an injection medical device is also disclosed.

10 Claims, 2 Drawing Sheets

(56) References Cited

U.S. PATENT DOCUMENTS

| | | | | |
|---|---|---|---|---|
| 8,695,530 B2* | 4/2014 | Sun | ................ | B05C 13/02 |
| | | | | 427/2.24 |
| 8,757,219 B2* | 6/2014 | Pacetti | ................ | B65B 31/044 |
| | | | | 623/1.1 |
| 9,084,874 B2* | 7/2015 | Nguyen | ................ | B05C 5/02 |
| 9,242,265 B2* | 1/2016 | Hedges | ................ | B41J 3/4073 |
| 9,283,350 B2* | 3/2016 | Chappa | ................ | A61M 25/0009 |
| 9,433,963 B2* | 9/2016 | Urquhart | ................ | B05B 15/55 |
| 9,789,505 B2* | 10/2017 | Kimpel, Jr. | ................ | B05B 7/166 |
| 10,022,476 B2* | 7/2018 | Zhang | ................ | A61M 25/0009 |
| 10,086,399 B2* | 10/2018 | Moser | ................ | B05C 17/00576 |
| 10,166,567 B2* | 1/2019 | Kimpel | ................ | B05B 13/0207 |
| 10,288,771 B1* | 5/2019 | Kester | ................ | G02B 1/11 |
| 10,328,448 B2* | 6/2019 | Urquhart | ................ | B05B 15/55 |
| 10,441,679 B2* | 10/2019 | Gross | ................ | A61L 27/46 |
| 10,661,296 B2* | 5/2020 | Urquhart | ................ | B05C 5/02 |
| 10,730,103 B2* | 8/2020 | Hosek | ................ | H01F 1/24 |
| 10,850,302 B2* | 12/2020 | Ito | ................ | B05D 1/26 |
| 10,875,048 B2* | 12/2020 | Surma | ................ | B05C 3/10 |
| 10,894,270 B2* | 1/2021 | Tagawa | ................ | B05C 5/00 |
| 11,213,849 B2* | 1/2022 | Choi | ................ | B05C 9/14 |
| 11,285,507 B2* | 3/2022 | Choi | ................ | B05C 13/02 |
| 11,623,273 B2* | 4/2023 | Hosek | ................ | B05C 5/001 |
| | | | | 419/26 |
| 11,819,590 B2* | 11/2023 | Militello | ................ | B05C 21/00 |
| 2001/0008649 A1 | 7/2001 | Layrolle et al. | | |
| 2005/0279639 A1 | 12/2005 | Shrewsburg et al. | | |
| 2011/0020531 A1 | 1/2011 | Larson et al. | | |
| 2014/0277023 A1* | 9/2014 | Sekino | ................ | B05B 17/04 |
| | | | | 239/128 |
| 2018/0036756 A1* | 2/2018 | Power | ................ | B05B 12/1418 |
| 2019/0216985 A1* | 7/2019 | McBurney | ................ | C08L 1/286 |
| 2020/0246604 A1* | 8/2020 | Asefi | ................ | A61M 1/916 |
| 2020/0360572 A1* | 11/2020 | Militello | ................ | B05C 13/025 |
| 2021/0030397 A1* | 2/2021 | Lee | ................ | A61B 90/94 |
| 2021/0220866 A1* | 7/2021 | Chappa | ................ | B05B 15/20 |
| 2021/0341370 A1* | 11/2021 | Luthe | ................ | B01D 49/006 |
| 2021/0386917 A1* | 12/2021 | Burgmeier | ................ | A61L 29/085 |
| 2022/0054666 A1* | 2/2022 | Phillips | ................ | A61M 16/201 |
| 2024/0050979 A1* | 2/2024 | Tacchini | ................ | B05B 7/166 |

\* cited by examiner

APPARATUS AND METHOD FOR COATING AN INJECTION MEDICAL DEVICE

CROSS REFERENCES

This application is a U.S. Application claiming priority to Italian Application No. 102022000017178 filed on Aug. 11, 2022, the disclosure of which is incorporated herein by reference in its entirety.

TECHNICAL FIELD

The present disclosure relates to an apparatus for coating an injection medical device and a method for coating such an injection medical device.

BACKGROUND

As is well known, injection medical devices are widely used in the medical field. They generally comprise a glass cylinder having an inner surface coated with a coating layer and a sealing plunger in sliding engagement within the glass cylinder to deliver a drug to a patient by an injection.

Such medical injection devices include syringes, cartridges but also auto-injectors or automatic injectors used for the subcutaneous and/or intravenous administration of drugs.

In this type of device, both to obtain the desired sliding properties of the plunger inside the cylinder of the injection medical device, e.g. the cylinder of a syringe, preventing abrasion of the cylinder surface of the syringe, and to provide a layer of protection between the drug and the cylinder, the inner surface of the syringe cylinder is typically coated with a lubricating coating substance, which is typically silicone oil-based.

To apply the coating substance, apparatuses are used which essentially consist of an inlet tank which can be filled with the coating substance, a delivery nozzle connected to the inlet tank and configured to deliver the coating substance nebulising it by the supply of compressed air, and a pump which is operationally interposed between the inlet tank and the delivery nozzle and configured to pump the coating substance towards the delivery nozzle.

The coating substance delivered on the injection medical device must necessarily be sterile, that is free of biological contaminants. Typically, a pre-sterilised coating substance is introduced into the inlet tank. The coating substance is thus sterilised on-site before it is introduced into the inlet tank, or it is purchased already pre-sterilised.

The Applicant has noted that sterilising the coating substance before introducing it into the inlet tank causes a burden on the operators. Furthermore, handling the coating substance for its sterilisation before introducing it into the inlet tank causes a risk of contact of the coating substance with biological contaminants, with consequent contamination of the coating substance.

The Applicant has also found that purchasing a pre-sterilised coating substance leads to increased costs and contamination risks of the coating substance in the time which passes between the supply of supplying the coating substance and its introduction into the inlet tank.

The Applicant has therefore felt the need to adopt precautions in handling the coating substance before and during the introduction thereof into the inlet tank.

The Applicant has realised that if an unsterilised coating substance is introduced in the inlet tank and the coating substance is sterilised while it is being supplied from the inlet tank to the delivery nozzle, both the supply of an unsterilised coating substance and the sterilisation of the coating substance prior to introduction into the inlet tank could be avoided. Furthermore, all the precautions which must be adopted to eliminate the risk of contamination of the coating substance during its introduction into the inlet tank could be avoided.

SUMMARY

The present disclosure therefore relates, in a first aspect thereof, to an apparatus for coating an injection medical device that includes an inlet tank fillable with a coating substance, a delivery nozzle configured to deliver the coating substance to an injection medical device, and a supply assembly interposed between, and in fluid communication with, the inlet tank and the delivery nozzle, the supply assembly being configured to withdraw the coating substance from the inlet tank and to supply it to the delivery nozzle. The supply assembly includes at least one sterilisation filter configured to filter the coating substance withdrawn from the inlet tank.

According to this disclosure, the inlet tank may be filled with an unsterilised coating substance. The filling of the inlet tank is thus simplified and speeded up, as it is not necessary to adopt precautions to avoid contaminating the coating substance with biological contaminants.

The/each sterilisation filter filters the coating substance while it is supplied by the inlet tank to the delivery nozzle, removing the biological contaminants therefrom. Therefore, the filtering of the coating substance occurs automatically and does not require any additional operations by the operator, apart from the introduction of the coating substance into the inlet tank. Furthermore, the positioning of the sterilisation filter(s) in the supply assembly ensures that the coating substance does not come into contact with the external environment after sterilisation, eliminating any risk of contamination with biological contaminants.

In a second aspect thereof, the present disclosure relates to a method for coating an injection medical device that includes the steps of introducing a coating substance into an inlet tank; withdrawing the coating substance from the inlet tank; filtering the coating substance after it has been withdrawn from the inlet tank; supplying the coating substance to a delivery nozzle after the coating substance has been filtered; nebulising the coating substance into the delivery nozzle; delivering the coating substance onto an injection medical device by the delivery nozzle after the coating substance has been nebulised; and wherein filtering the coating substance is performed by at least one sterilisation filter.

Throughout the present description and the appended claims, the term “sterilisation filter” is used to indicate a filter having a mesh size fine enough to intercept and capture at least 99% of the bacteria present in the coating substance, preferably substantially 100%.

The expression “fluid communication,” referred to two or more components, is used to indicate that such components are hydraulically connected so that a fluid can pass from one component to the other, possibly after opening any valves interposed between the components.

The term “thermally insulating material” is used to indicate a material having a thermal conductivity equal to or less than $$1\frac{W}{mK}.$$

In at least one of the aforementioned aspects, the present disclosure may comprise one or more of the following features, taken individually or possibly combined with each other.

Preferably, the entire apparatus of the disclosure, or at least the part of the apparatus that is upstream of the sterilisation filter(s), is arranged within a laminar flow hood, so as to fall within the environmental class suitable for the production of sterile components (class 5 of ISO 14644-1 standard).

Preferably, the inlet tank is maintained at room temperature.

Preferably, the coating substance is fed into the inlet tank at room temperature.

Preferably, the coating substance is kept at room temperature in the inlet tank.

Preferably, a service member is provided which is configured to pressurise the coating substance in the inlet tank.

Preferably, the service member is configured to provide the coating substance which is in the inlet tank with a pressure that is sufficient to move the coating substance from the inlet tank towards the sterilisation filter(s).

More preferably, the service member is configured to move the coating substance from the inlet tank through the sterilisation filter(s).

Preferably, the coating substance has a viscosity greater than 10000 cSt.

More preferably, the coating substance has a viscosity less than 15000 cSt.

In particularly preferred embodiments, the viscosity is comprised between 11000 cSt and 14000 cSt, more preferably between 12000 cSt and 13000 cSt, e.g., about 12500 cSt.

The Applicant has found that by delivering a coating substance whose viscosity is one order of magnitude greater than the typically adopted viscosity of about 1000 cSt on the injection medical device, the coating obtained in the injection medical device maintains its lubricating properties more effectively over time and the possibility of the coating substance to release particles into the injection medical device, thus altering the properties of the medical product to be injected by the injection medical device, is reduced.

Preferably, the inlet tank comprises at least one transparent wall portion through which the level of the coating substance inside the inlet tank can be checked, without the need to open the inlet tank.

Preferably, the at least one sterilisation filter has a mesh size less than 0.50 μm.

Preferably, the at least one sterilisation filter has a mesh size greater than 0.08 μm.

In particularly preferred embodiments, the mesh size of the at least one sterilisation filter is comprised between 0.10 μm and 0.35 μm, more preferably between 0.20 μm and 0.24 μm, e.g., about 0.22 μm.

Preferably, the supply assembly comprises a supply pump interposed between, and in fluid communication with, the at least one sterilisation filter and the delivery nozzle, the supply pump being configured to pump the coating substance towards the delivery nozzle.

Preferably, the supply pump is a pump of the volumetric type.

Preferably, the supply assembly comprises a plurality of heating elements configured to heat the coating substance withdrawn from the inlet tank prior to being delivered by the delivery nozzle. Indeed, the Applicant has found that when heated the coating substance flows more easily through the various conduits and the various components of the apparatus of the present disclosure, especially when, as in the preferred embodiments of the disclosure, a high-viscosity coating substance is used.

Preferably, the supply assembly comprises a first storage tank interposed between, and in fluid communication with, a first sterilisation filter and the delivery nozzle, wherein the first storage tank is configured to receive and temporarily store the coating substance withdrawn from the inlet tank and intended to be supplied to the delivery nozzle.

Preferably, the first storage tank can be configured in a filling condition in which the first storage tank receives and stores the coating substance withdrawn from the inlet tank.

The possibility to store the already sterilised coating substance in the first storage tank allows the coating substance to be supplied to the delivery nozzle while operations are being carried out on the inlet tank (e.g., cleaning or filling operations) or on the first sterilisation filter (e.g., cleaning or replacement operations).

Preferably, a first fill level detector is provided which is configured to measure the level of the coating substance in the first storage tank.

Preferably, the first fill level detector comprises a load cell configured to measure the pressure of the coating substance in the first storage tank.

Preferably, the first storage tank can be configured in a depressurisation condition in which the coating substance stored in the first storage tank is maintained at a pressure less than the atmospheric pressure.

Preferably, such pressure is comprised between 50 mbar and 400 mbar, more preferably between 100 mbar and 300 mbar, e.g., about 200 mbar.

Depressurising the coating substance in the first storage tank for a certain period of time allows to remove any bubbles formed following the passage of the coating substance through the first sterilisation filter. Such an expedient is particularly useful when the coating substance has a particularly high viscosity, a circumstance which makes the formation of bubbles more likely.

Preferably, when the first storage tank is in the depressurisation condition it is tightly sealed off with respect to the other components of the apparatus of the disclosure.

Preferably, the first storage tank can be configured in a heating condition in which the coating substance stored in the first storage tank is heated up to a temperature of 100° C. or higher, preferably 120° C.

Heating the coating substance in the first storage tank improves the rheological properties of the coating substance, especially if the coating substance has a high viscosity, and facilitates its supply to the delivery nozzle. The improved rheological properties of the coating substance allow to deliver it from the delivery nozzle more uniformly and precisely, thereby obtaining a uniform and thin layer of coating substance on the medical device.

Preferably, the supply assembly comprises at least one first heating element configured to heat the coating substance stored in the first storage tank.

The first heating element can be any element configured to release thermal energy and placed in a heat exchange relationship with the coating substance stored in the first storage tank.

Preferably, the at least one first heating element is arranged inside a first insulating jacket made at least partially of a thermally insulating material and placed outside the first storage tank.

The first heating element may comprise, for example, one or more electrical resistors or one or more conduits formed in, or associated with, the first insulating jacket and in which heating fluid circulates.

In alternative embodiments, the first heating element is a heating coil (e.g., an electrical resistor or a conduit in which a suitable heating fluid circulates) placed inside the first storage tank.

Preferably, the first storage tank is removable from the first insulating jacket.

In this way it is possible to easily perform maintenance or cleaning operations on the first storage tank.

Preferably, a first temperature sensor is associated with the first storage tank, so that the temperature reached by the coating substance inside the first storage tank can be monitored.

Preferably, the first storage tank can be configured in a supply condition in which the coating substance stored in the first storage tank is withdrawn from the first storage tank to be supplied to the delivery nozzle.

Preferably, in the aforementioned supply condition, the coating substance stored in the first storage tank is brought to a pressure greater than the atmospheric pressure.

Preferably, such pressure is less than 2.5 bar, more preferably less than 2 bar.

In this way the exit of the coating substance from the first storage tank is facilitated and the risk of cavitation of the supply pump is reduced.

Preferably, the first storage tank is selectively configurable in the filling condition or in the supply condition.

Preferably, the first storage tank is selectively configurable in the filling condition or in the depressurisation condition or in the heating condition or in the supply condition.

Preferably, the supply assembly comprises a second storage tank interposed between, and in fluid communication with, a second sterilisation filter and the delivery nozzle, wherein the second storage tank is configured to receive and temporarily store the coating substance withdrawn from the inlet tank and intended to be supplied to the delivery nozzle.

Preferably, the second storage tank can be configured in a filling condition in which the second storage tank receives and stores the coating substance withdrawn from the inlet tank.

The possibility to store the already sterilised coating substance in the second storage tank allows to supply the coating substance from the inlet tank to the second storage tank while the first storage tank is in an unsuitable condition to receive the coating substance, e.g., in a depressurisation, heating or supply condition. Furthermore, it is possible to supply the coating substance to the delivery nozzle from the second storage tank while the first storage tank is filled with further coating substance, or during a possible replacement of the first storage tank, or while operations are performed on the inlet tank (e.g. cleaning or filling operations) or on the first sterilisation filter (e.g. cleaning or replacement operations).

The provision of two storage tanks therefore allows one of such storage tanks to be filled with coating substance coming from the inlet tank, or cleaning or replacement operations to be carried out on such a storage tank, or on the respective sterilisation filter if a respective sterilisation filter is provided upstream of each storage tank, while the other previously filled storage tank supplies the coating substance to the delivery nozzle and vice versa, thus achieving a substantially continuous supply of coating substance to the delivery nozzle.

In some embodiments, the supply assembly comprises a single sterilisation filter arranged downstream of the inlet tank and upstream of the two storage tanks.

Preferably, a second fill level detector is provided which is configured to measure the level of the coating substance in the second storage tank.

Preferably, the second fill level detector comprises a load cell configured to measure the pressure of the coating substance in the second storage tank.

Preferably, the second storage tank can be configured in a depressurisation condition in which the coating substance stored in the second storage tank is maintained at a pressure less than the atmospheric pressure.

Preferably, such pressure is comprised between 50 mbar and 400 mbar, more preferably comprised between 100 mbar and 300 mbar, e.g., about 200 mbar.

The depressurisation of the coating substance in the second storage tank allows the removal of bubbles formed following the passage of the coating substance through the second sterilisation filter or through the single sterilisation filter which might be provided upstream of the two storage tanks.

Preferably, when the second storage tank is in the depressurisation condition it is tightly sealed off with respect to the other components of the apparatus of the disclosure.

Preferably, the second storage tank can be configured in a heating condition in which the coating substance stored in the second storage tank is heated up to a temperature of 100° C. or higher, preferably 120° C.

Heating the coating substance in the second storage tank improves the rheological properties of the coating substance, as described above with reference to the first storage tank.

Preferably, the supply assembly includes at least one second heating element configured to heat the coating substance stored in the second storage tank.

The second heating element may be any element configured to release thermal energy and placed in a heat exchange relationship with the coating substance stored in the second storage tank.

Preferably, the at least one second heating element is arranged inside a second insulating jacket made at least partially of a thermally insulating material and placed outside the second storage tank.

The second heating element may comprise, for example, one or more electrical resistors or one or more conduits formed in, or associated with, the second insulating jacket and in which heating fluid circulates.

In alternative embodiments, the second heating element is a heating coil (e.g., an electrical resistor or a conduit in which a suitable heating fluid circulates) placed inside the second storage tank.

Preferably, the second storage tank is removable from the second insulating jacket, so that maintenance or cleaning operations can be performed, for example.

Preferably, a second temperature sensor is associated with the second storage tank, so that the temperature reached by the coating substance inside the second storage tank can be monitored.

Preferably, the second storage tank can be configured in a supply condition in which the coating substance stored in the second storage tank is withdrawn from the second storage tank to be supplied to the delivery nozzle.

The coating substance, properly filtered, degassed and heated, can thus be supplied to the delivery nozzle from the second storage tank while the first storage tank is in the filling, depressurisation or heating condition.

Preferably, in the aforementioned supply condition, the coating substance stored in the second storage tank is brought to a pressure greater than the atmospheric pressure.

Preferably, such pressure is less than 2.5 bar, more preferably less than 2 bar, so as to facilitate the exit of the coating substance from the second storage tank and reduce the risk of cavitation of the supply pump.

Preferably, the second storage tank is selectively configurable in the filling condition or in the supply condition.

Preferably, the second storage tank is selectively configurable in the filling condition or in the depressurisation condition or in the heating condition or in the supply condition.

Preferably, a control unit is operatively connected to the first storage tank and second storage tank.

Preferably, the control unit is configured to set in the first storage tank the supply condition when the second storage tank is in the filling condition.

Preferably, the control unit is configured to set in the first storage tank the supply condition when the second storage tank is in the depressurisation condition.

Preferably, the control unit is configured to set in the first storage tank the supply condition when the second storage tank is in the heating condition.

Preferably, the control unit is configured to set in the second storage tank the supply condition when the first storage tank is in the filling condition.

Preferably, the control unit is configured to set in the second storage tank the supply condition when the first storage tank is in the depressurisation condition.

Preferably, the control unit is configured to set in the second storage tank the supply condition when the first storage tank is in the heating condition.

Preferably, the control unit is configured to control the first heating element based on signals received from the first temperature sensor.

Preferably, the control unit is configured to control the second heating element based on signals received from the second temperature sensor.

Preferably, the control unit is configured to switch from the heating condition to the supply condition of the first storage tank based on signals received from the first temperature sensor.

Preferably, the control unit is configured to switch from the heating condition to the supply condition of the second storage tank based on signals received from the second temperature sensor.

Preferably, the control unit is configured to switch from the filling condition to the depressurisation condition of the first storage tank based on signals received from the first fill level detector.

Preferably, the control unit is configured to switch from the filling condition to the depressurisation condition of the second storage tank based on signals received from the second fill level detector.

Preferably, the control unit is configured to switch from the supply condition to the filling condition of the first storage tank based on signals received from the first fill level detector.

Preferably, the control unit is configured to switch from the supply condition to the filling condition of the second storage tank based on signals received from the second fill level detector.

Preferably, the supply assembly comprises a first fluid circuit having a first end coupled to the inlet tank, a second end coupled to the first storage tank and a third end coupled to the second storage tank.

Preferably, the supply assembly comprises a second fluid circuit having a first end coupled to the first storage tank, a second end coupled to the second storage tank and a third end coupled to the delivery nozzle.

Preferably, the first fluid circuit comprises a first conduit that connects the inlet tank to the first sterilisation filter, a second conduit that connects the first sterilisation filter to the first storage tank, a third conduit that connects the inlet tank to the second sterilisation filter, and a fourth conduit that connects the second sterilisation filter to the second storage tank.

Preferably, the first conduit and the third conduit can be entirely separate from each other or share a common conduit branch.

Preferably, the supply pump belongs to the second fluid circuit.

Preferably, a first conduit of the second fluid circuit connects the first storage tank to the supply pump.

Preferably, a second conduit of the second fluid circuit connects the second storage tank to the supply pump.

Preferably, a third conduit of the second fluid circuit connects the supply pump to the delivery nozzle.

Preferably, the supply assembly comprises at least one insulation jacket removably placed around at least part of the second fluid circuit.

The possibility of removing the insulation jacket from the part of the second fluid circuit on which it is placed allows an easy disassembly of such a part of circuit, such disassembly being necessary to be able to perform periodic cleaning operations on this part of circuit. Such periodic cleaning is particularly necessary when the coating substance used is high-viscosity silicone.

Preferably, the supply assembly includes at least one third heating element configured to heat at least part of the second fluid circuit.

The third heating element allows to keep the coating substance in the second fluid circuit at a temperature such as to optimise the rheological properties of the coating substance, promoting the flow thereof in the second fluid circuit and a uniform spraying from the delivery nozzle.

Preferably, the at least one third heating element is arranged inside the at least one insulation jacket.

Preferably, the at least one third heating element comprises an electrical resistor.

Preferably, the supply assembly comprises at least one temperature sensor associated with the insulation jacket.

Preferably, the temperature sensor is integrated in the at least one insulation jacket.

Preferably, the control unit is configured to control the at least one third heating element based on signals received by the respective temperature sensor.

In particularly preferred embodiments, a first insulation jacket is provided on the first conduit of the second fluid circuit.

Preferably, a second insulation jacket is provided on the second conduit of the second fluid circuit.

Preferably, a third insulation jacket is provided on the third conduit of the second fluid circuit.

Thus, all the conduits that connect the first storage tank and the second storage tank to the supply pump and the latter to the delivery nozzle can be disassembled and possibly replaced or reassembled after being cleaned thanks to the provision on each of such conduits of a respective removable insulation jacket.

Preferably, the first conduit and the second conduit of the second fluid circuit have equal length.

Preferably, the first conduit and the second conduit of the second fluid circuit have equal fluid passage sections.

Preferably, the first conduit and the second conduit of the second fluid circuit have a constant fluid passage section along them.

In this way, the properties of the coating substance which is supplied to the delivery nozzle from the first storage tank or the second storage tank do not change.

Preferably, when the coating substance is fed into the inlet tank, the inlet tank is at atmospheric pressure.

Preferably, withdrawing the coating substance from the inlet tank comprises pressurising the inlet tank.

Preferably, filtering the coating substance after it has been withdrawn from the inlet tank comprises passing the coating substance through the sterilisation filter due to the pressurisation of the inlet tank.

Preferably, the coating substance withdrawn from the inlet tank is heated when it is supplied to the delivery nozzle while maintaining the inlet tank at room temperature.

Preferably, the coating substance withdrawn from the inlet tank is filtered while maintaining it at room temperature, and then heated.

Preferably, the coating substance withdrawn from the inlet tank and intended to be supplied to the delivery nozzle is selectively introduced into the first storage tank or the second storage tank.

Preferably, the selective feeding of the coating substance into the first storage tank or the second storage tank occurs due to the pressurisation of the inlet tank.

Preferably, the coating substance stored in the first storage tank is kept at a value less than 2.5 bar, more preferably less than 2 bar, when the coating substance is supplied to the delivery nozzle from the first storage tank.

Preferably, the pressure of the coating substance stored in the first storage tank is maintained at a value greater than the atmospheric pressure when the coating substance is supplied to the delivery nozzle from the first storage tank.

Preferably, the pressure of the coating substance stored in the second storage tank is kept at a value less than 2.5 bar, more preferably less than 2 bar, when the coating substance is supplied to the delivery nozzle from the second storage tank.

Preferably, the pressure of the coating substance stored in the second storage tank is maintained at a value greater than the atmospheric pressure when the coating substance is supplied to the delivery nozzle from the second storage tank.

Preferably, supplying the coating substance to the delivery nozzle comprises supplying the coating substance to the delivery nozzle selectively from the first storage tank or from the second storage tank.

Preferably, before supplying the coating substance to the delivery nozzle from the first storage tank, a depressurisation condition is created in the first storage tank.

Preferably, creating a depressurisation condition in the first storage tank comprises bringing the pressure of the coating substance in the first storage tank to a value less than the atmospheric pressure, preferably comprised between 50 mbar and 400 mbar, even more preferably comprised between 100 mbar and 300 mbar, e.g., about 200 mbar.

Preferably, the depressurisation condition in the first storage tank is maintained for a time comprised between 5 and 30 minutes.

Preferably, a single depressurisation cycle is carried out in the first storage tank, in which case the pressurisation condition is maintained for a minimum time of 20 minutes.

Alternatively, several depressurisation cycles (e.g., 3-4 cycles) can be carried out in the first storage tank, in which case in each of the depressurisation cycles the pressurisation condition is maintained for about 5 minutes.

Preferably, before creating the depressurisation condition in the first storage tank, the first storage tank is tightly sealed off from the inlet tank and from the delivery nozzle.

Preferably, before supplying the coating substance to the delivery nozzle from the second storage tank, a depressurisation condition is created in the second storage tank.

Preferably, creating a depressurisation condition in the second storage tank comprises bringing the pressure of the coating substance in the second storage tank to a value less than the atmospheric pressure, preferably comprised between 50 mbar and 400 mbar, even more preferably comprised between 100 mbar and 300 mbar, e.g., about 200 mbar.

Preferably, the depressurisation condition in the second storage tank is maintained for a time comprised between 5 and 30 minutes.

Preferably, a single depressurisation cycle is carried out in the second storage tank, in which case the pressurisation condition is maintained for a minimum of 20 minutes.

Alternatively, several depressurisation cycles (e.g., 3-4 cycles) can be carried out in the second storage tank, in which case in each of the depressurisation cycles the pressurisation condition is maintained for about 5 minutes.

Preferably, before creating the depressurisation condition in the second storage tank, the second storage tank is tightly sealed off from the inlet tank and from the delivery nozzle.

Preferably, the first storage tank is heated before supplying the coating substance to the delivery nozzle from the first storage tank.

Preferably, the coating substance stored in the first storage tank is heated to a temperature of 100° C. or higher, more preferably 120° C., before supplying the coating substance to the delivery nozzle from the first storage tank.

Preferably, the second storage tank is heated before supplying the coating substance to the delivery nozzle from the second storage tank.

Preferably, the coating substance stored in the second storage tank is heated to a temperature of 100° C. or higher, more preferably 120° C., before supplying the coating substance to the delivery nozzle from the second storage tank.

Preferably, the first storage tank is heated after having created in the first storage tank the depressurisation condition.

Preferably, the second storage tank is heated after having created in the second storage tank the depressurisation condition.

Preferably, supplying the coating substance to the delivery nozzle from the first storage tank comprises pressurising the first storage tank after having created the depressurisation condition in the first storage tank.

Preferably, supplying the coating substance to the delivery nozzle from the second storage tank comprises pressurising the second storage tank after having created the depressurisation condition in the second storage tank.

These aspects are merely illustrative aspects of the innumerable aspects associated with the present disclosure and should not be deemed as limiting in any manner. These and other aspects, features and advantages of the present disclosure will become apparent from the following detailed description when taken in conjunction with the referenced figures.

BRIEF DESCRIPTION OF THE DRAWINGS

The features and advantages of the present disclosure will result from the following detailed description of some examples embodiments thereof, provided by way of non-limiting example only, such a description being conducted referring to the appended drawings, in which.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. The following definitions and non-limiting guidelines must be considered in reviewing the description of the technology set forth herein.

In the following detailed description numerous specific details are set forth in order to provide a thorough understanding of the present disclosure. However, it will be understood by those skilled in the art that the present disclosure may be practiced without these specific details. For example, the present disclosure is not limited in scope to the particular type of industry application depicted in the figures. In other instances, well-known methods, procedures, and components have not been described in detail so as not to obscure the present disclosure.

The headings and sub-headings used herein are intended only for general organization of topics within the present disclosure and are not intended to limit the disclosure of the technology or any aspect thereof. In particular, subject matter disclosed in the "Background" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

The citation of references herein does not constitute an admission that those references are prior art or have any relevance to the patentability of the technology disclosed herein. All references cited in the "Detailed Description" section of this specification are hereby incorporated by reference in their entirety.

Figure 1:
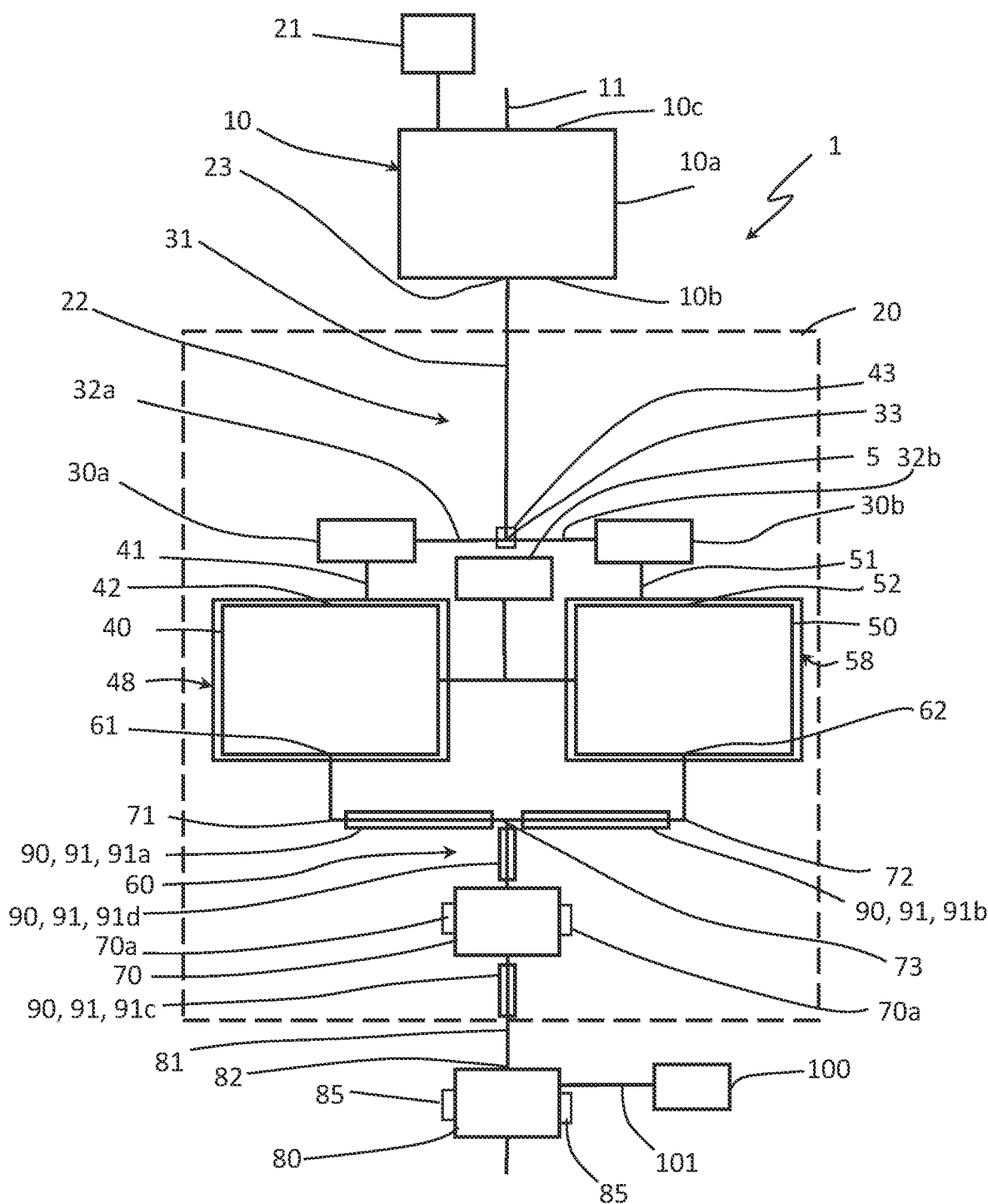
FIG. 1 shows a schematic view of an apparatus for coating an injection medical device in accordance with an embodiment of the present disclosure.

An apparatus for coating an injection medical device, which is the subject matter of the present disclosure, is schematically shown in FIG. 1 and is indicated by numerical reference 1.

The apparatus 1 comprises an inlet tank 10 that can be filled with a coating substance by an operator.

The inlet tank 10 comprises an access sleeve 11 through which the coating substance can be fed.

The access sleeve 11 is configured to allow a tight sealed insulation of the inlet tank 10 by, for example, the closure of a special valve, not shown.

The apparatus 1, or at least the inlet tank 10 and the access sleeve 11, is/are arranged inside a laminar flow hood.

The inlet tank 10 comprises a side wall 10a, preferably cylindrical. At least part of the side wall 10a is made of at least partially transparent material, for example glass, so that the operator can check the level of the coating substance inside the inlet tank 10 without having to open it. The side wall 10a has a graduated scale adapted to allow the amount of coating substance inside the inlet tank 10 to be measured.

The inlet tank 10 further comprises a lower wall 10b and an upper wall 10c, preferably made of stainless steel. The side wall 10a extends between the lower wall 10b and the upper wall 10c.

The inlet tank 10 is configured to gradually release the coating substance. The inlet tank 10 is kept at room temperature. The coating substance is fed therein at room temperature and is maintained at room temperature.

The apparatus 1 comprises a supply assembly 20 configured to withdraw the coating substance from the inlet tank 10.

A service member 21 is associated with inlet tank 10.

The service member 21 is configured to pressurise the coating substance in the inlet tank 10 so as to make it flow out into the supply assembly 20.

The service member 21 comprises, for example, a pressure pump or a compressed air line connected to a compressor.

The supply assembly 20 comprises a first fluid circuit 22 in fluid communication with the inlet tank 10 to receive the coating substance flowing out therefrom. In particular, the first fluid circuit 22 comprises a first end 23 at which the first fluid circuit 22 is connected to the inlet tank 10.

The supply assembly 20 further comprises a first sterilisation filter 30a configured to filter the coating substance withdrawn from the inlet tank 10. The first sterilisation filter 30a is configured to remove biological contaminants from the coating substance, preferably in their entirety.

In the preferred embodiment, the first sterilisation filter 30a has a mesh size of 0.22 μm (micrometre).

The first sterilisation filter 30a is placed in the first fluid circuit 22, in fluid communication with the inlet tank 10 through a first conduit having a first conduit branch 31 extended from the inlet tank 10 to a first junction 33 and a second conduit branch 32a extended from the first junction 33 to the first sterilisation filter 30a.

The first conduit branch 31 and the second conduit branch 32a are preferably made of stainless steel or of a temperature-resistant plastic material, e.g., PTFE (polytetrafluoroethylene) or FEP (fluorinated ethylene propylene).

The service member 21 is configured to provide the coating substance with a pressure that is sufficient to make it pass through the first sterilisation filter 30a with a predetermined flow rate.

Figure 2:
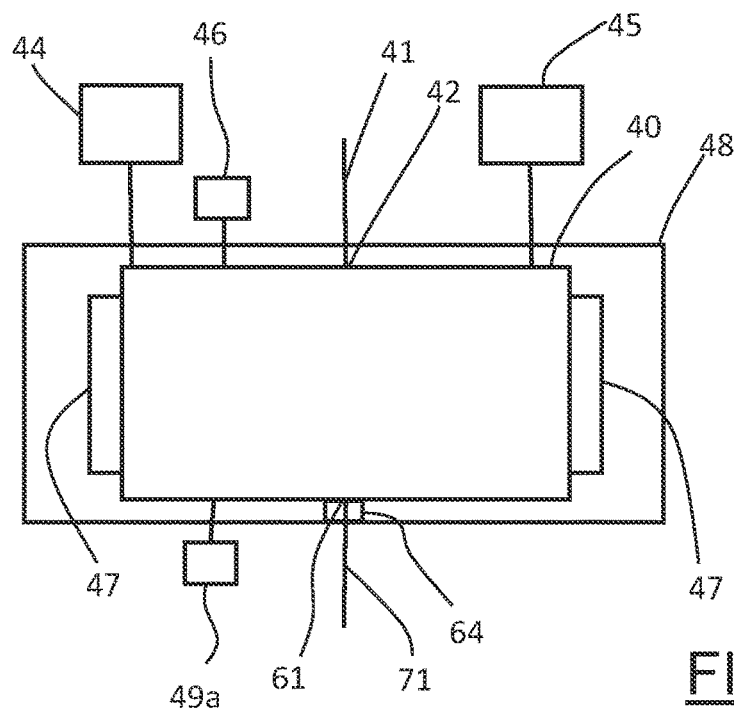
FIG. 2 shows a schematic view of a first detail of the apparatus of FIG. 1.

The supply assembly 20 further comprises a first storage tank 40, schematically shown in FIG. 2 and preferably made of stainless steel.

The first storage tank 40 is placed downstream of the first sterilisation filter 30a and in fluid communication with the inlet tank 10 through the first sterilisation filter 30a, so that it can temporarily store the coating substance withdrawn from the inlet tank 10 and filtered by the first sterilisation filter 30a.

The first fluid circuit 22 comprises a second conduit 41 extended from the first sterilisation filter 30a to the first storage tank 40 to put the first sterilisation filter 30a in fluid communication with the first storage tank 40. The first fluid circuit 22 further comprises a second end 42 at which the first fluid circuit 22 is connected to the first storage tank 40 and through which the coating substance is fed into the first storage tank 40.

The second conduit 41 is preferably made of stainless steel or of a temperature-resistant plastic material, e.g., PTFE or FEP.

The pressure provided to the coating substance by the service member 21 allows the coating substance to flow from the inlet tank 10 through the first conduit branch 31, the second conduit branch 32a, the first sterilisation filter 30a and the second conduit 41 until it reaches the first storage tank 40.

A first pressurisation member 44, for example a pressure pump or a compressed air line in communication with a compressor, is associated with the first storage tank 40 to pressurise the coating substance stored in the first storage tank 40 in a selective and controlled manner. In particular, the first pressurisation member 44 is configured to pressurise the coating substance in the first storage tank 40 to a pressure greater than the atmospheric pressure and less than 2.5 bar, preferably less than 2 bar.

A first depressurisation member 45, e.g., a vacuum pump, is associated with the first storage tank 40 to depressurise the coating substance stored in the first storage tank 40 in a selective and controlled manner. In particular, the first depressurisation member 45 is configured to depressurise the coating substance in the first storage tank 40 to bring it to a pressure less than the atmospheric pressure, preferably comprised between 50 mbar and 400 mbar, more preferably comprised between 100 mbar and 300 mbar, e.g., about 200 mbar.

The first storage tank 40 comprises a first fill level detector 46 configured to detect the fill level of the first storage tank 40. The first fill level detector 46 may comprise, for example, a load cell configured to measure the pressure of the coating substance in the first storage tank 40.

A first heating element 47 is associated with the first storage tank 40 to heat the first storage tank 40 and the coating substance contained therein in a selective and controlled manner. The first heating element 47 is removably mounted on the first storage tank 40, preferably outside the first storage tank 40.

In the preferred embodiment, the first heating element 47 is integrated in a first insulating jacket 48, which is made at least partially of a thermally insulating material and is placed outside the first storage tank 40. The first heating element 47 may comprise, for example, electrical resistors or heating conduits (coils) in which a heating fluid circulates.

The first insulating jacket 48 is configured to thermally insulate the first storage tank 40 so as not to dissipate the heat provided by the first heating element 47. The first storage tank 40 can be removed from the first insulating jacket 48, e.g., to carry out maintenance or cleaning operations.

A first temperature sensor 49a is associated with the first insulating jacket 48, and thus with the first storage tank 40, to monitor the temperature of the first insulating jacket 48, and thus of first storage tank 40 and of the coating substance contained in the first storage tank 40. Preferably, the first temperature sensor 49a comprises a temperature sensor placed inside the first insulating jacket 48 to check that the temperature of the coating substance contained in the first storage tank 40 reaches 120° C.

Figure 3:
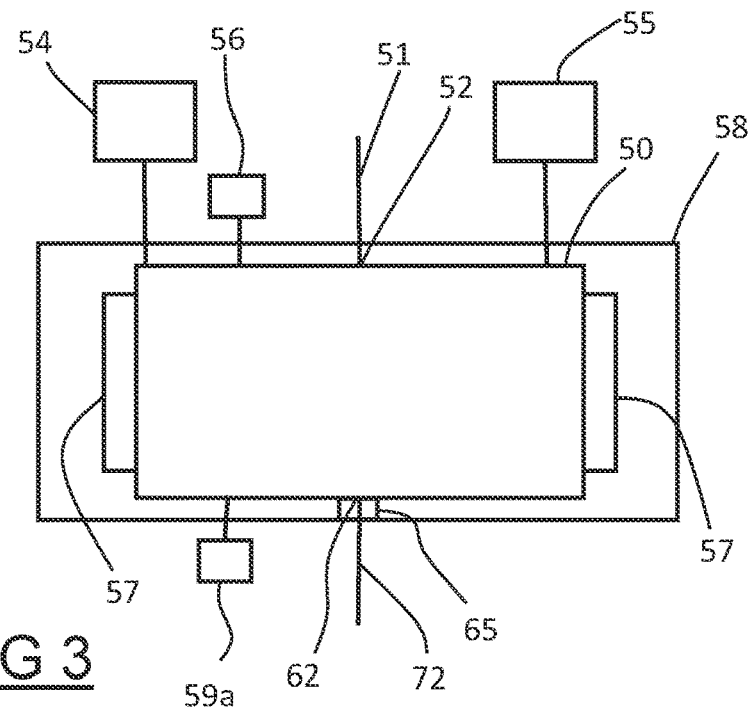
FIG. 3 shows a schematic view of a second detail of the apparatus of FIG. 1.

The supply assembly 20 further comprises a second sterilisation filter 30b and a second storage tank 50 placed downstream of the second sterilisation filter 30b. The second sterilisation filter 30b and the second storage tank 50 are schematically shown in FIG. 3 and are analogous to the first sterilisation filter 30a and the first storage tank 40, respectively.

The second sterilisation filter 30b is configured to filter the coating substance withdrawn from the inlet tank 10 and supplied to the second storage tank 50.

Like the first sterilisation filter 30a, the second sterilisation filter 30b is also configured to eliminate biological contaminants from the coating substance, preferably in their entirety, and has a mesh size of 0.22 μm.

The second sterilisation filter 30b is placed in the first fluid circuit 22, in fluid communication with the inlet tank 10 through a third conduit comprising the first conduit branch 31 extended from the inlet tank 10 to the first junction 33 and a third conduit branch 32b extended from the first junction 33 to the second sterilisation filter 30b.

The third conduit branch 32b is also preferably made of stainless steel or of a temperature-resistant plastic material, e.g., PTFE or FEP.

The service member 21 is configured to provide the coating substance with a pressure that is sufficient to make it pass through the second sterilisation filter 30b with a predetermined flow rate.

The second storage tank 50 is placed in fluid communication with the inlet tank 10 through the second sterilisation filter 30b. The second storage tank 50 is configured to temporarily store the coating substance withdrawn from the inlet tank 10 and filtered by the second sterilisation filter 30b.

In the preferred embodiment, the second storage tank 50 is made of stainless steel.

The first fluid circuit 22 comprises a fourth conduit 51 extended from the second sterilisation filter 30b to the second storage tank 50 to put the second sterilisation filter 30b in fluid communication with the second storage tank 50.

The second fluid circuit 22 further comprises a third end 52 at which the first fluid circuit 22 is connected to the second storage tank 50 and through which the coating substance is fed into the second storage tank 50.

The fourth conduit 51 is preferably made of stainless steel or of a temperature-resistant plastic material, e.g., PTFE or FEP.

The coating substance can be brought from the inlet tank 10 to the second storage tank 50. The pressure provided to the coating substance by the service member 21 allows the coating substance to flow from the inlet tank 10 through the first conduit branch 31, the third conduit branch 32b, the second sterilisation filter 30b and the fourth conduit 51 until it reaches the second storage tank 50.

In an embodiment not shown, apparatus 1 comprises a single sterilisation filter in place of the aforesaid two sterilisation filters 30a, 30b. Such a single sterilisation filter may be arranged in the first conduit branch 31 and the first junction 33 be placed between the aforementioned single sterilisation filter, the first storage tank 40 and the second storage tank 50. Alternatively, the aforementioned single sterilisation filter may be placed at the first junction 33. In both cases, the second conduit branch 32a and the second conduit 41 define a single conduit.

Through the first junction 33, the coating substance can be directed alternatively and in a controlled manner from the inlet tank 10 to the first storage tank 40, through the first conduit branch 31, the second conduit branch 32a, the first sterilisation filter 30a and the second conduit 41, or from the inlet tank 10 to the second storage tank 50, through the first conduit branch 31, the third conduit branch 32b, the second sterilisation filter 30b and the fourth conduit 51.

As shown in FIG. 1, the first fluid circuit 22 comprises an inlet valve 43, placed for example at the junction 33 and configured to isolate in a controlled manner either the first storage tank 40 or the second storage tank 50 from the first fluid circuit 22.

The inlet valve 43 is controlled to selectively direct the coating substance from inlet tank 10 to the first storage tank 40 or the second storage tank 50.

Preferably, the inlet valve 43 is a three-way valve.

Alternatively, a first inlet valve placed for example at the second end 42 and a second inlet valve placed for example at the third end 52 may be provided to isolate in a controlled manner the first storage tank 40 or the second storage tank 50, respectively, from the first fluid circuit 22.

A second pressurisation member 54, for example a pressure pump or a compressed air line in communication with a compressor, is associated with the second storage tank 50 to pressurise the coating substance stored in the second storage tank 50 in a selective and controlled manner. The second pressurisation member 54 is configured to pressurise the coating substance in the second storage tank 50 to a pressure greater than the atmospheric pressure and less than 2.5 bar, preferably less than 2 bar.

A second depressurisation member 55, e.g., a vacuum pump, is associated with the second storage tank 50 to depressurise the coating substance stored in the second storage tank 50 in a selective and controlled manner. The second depressurisation member 55 is configured to depressurise the coating substance in the second storage tank 50 to bring it to a pressure less than the atmospheric pressure, preferably comprised between 50 mbar and 400 mbar, even more preferably comprised between 100 mbar and 300 mbar, e.g., about 200 mbar.

The second storage tank 50 comprises a second fill level detector 56 configured to detect the fill level of the second storage tank 50. The second fill level detector 56 may comprise, for example, a load cell configured to measure the pressure of the coating substance in the second storage tank 50.

A second heating element 57 is associated with the second storage tank 50 to heat the coating substance contained therein in a controlled manner. The second heating element 57 is removably mounted on the second storage tank 50, preferably outside the second storage tank 50.

In the preferred embodiment, the second heating element 57 is integrated in a second insulating jacket 58, which is made at least partially of a thermally insulating material and is placed outside the second storage tank 50. The second heating element 57 may comprise, for example, electrical resistors or heating conduits (coils) in which a heating fluid circulates.

The second insulating jacket 58 is configured to thermally insulate the second storage tank 50 so as not to dissipate the heat provided by the second heating element 57. The second storage tank 50 can be removed from the second insulating jacket 58, for example to perform maintenance or cleaning operations.

A second temperature sensor 59a is associated with the second insulating jacket 58, and thus the second storage tank 50, to measure the temperature of the second insulating jacket 58, and thus of the second storage tank 50 and of the coating substance contained therein. Preferably, the second temperature sensor 59a comprises a temperature sensor placed inside the second insulating jacket 58 to check that the temperature of the coating substance contained in the second storage tank 50 reaches 120° C.

The supply assembly 20 further comprises a second fluid circuit 60 in fluid communication with the first storage tank 40 and with the second storage tank 50.

The second fluid circuit 60 comprises a first end 61 connected to the first storage tank 40 and a second end 62 connected to the second storage tank 50.

As shown in FIGS. 2 and 3, a first outlet valve 64 is arranged for example at the first end 61 and is configured to isolate the first storage tank 40 from the second fluid circuit 60 in a controlled manner. Similarly, a second outlet valve 65 is arranged for example at the second end 62 and is configured to isolate the second storage tank 50 from the second fluid circuit 60 in a controlled manner.

As shown in FIG. 1, the supply assembly 20 also comprises a supply pump 70 in fluid communication with the first storage tank 40 and with the second storage tank 50. The supply pump 70 is arranged in the second fluid circuit 60 and is, preferably, a volumetric pump.

In a preferred embodiment, the supply pump 70 comprises a respective heating element 70a configured to heat the coating substance within the pump. For example, the heating element 70a may comprise one or more electrical resistors applied on or integrated in a casing of the supply pump 70.

The second fluid circuit 60 comprises a first conduit 71 that connects the first storage tank 40 to the supply pump 70 and a second conduit 72 that connects the second storage tank 50 to a suction head of the supply pump 70.

The first conduit 71 and the second conduit 72 are preferably made of stainless steel or of a temperature-resistant plastic material, e.g., PTFE or FEP.

The first conduit 71 and the second conduit 72 converge in a second junction 73 placed between the first storage tank 40, the second storage tank 50 and the supply pump 70. The first conduit 71 and the second conduit 72 may comprise a common section between the second junction 73 and the supply pump 70, as shown in FIG. 1.

Preferably, the first conduit 71 and the second conduit 72 have equal length and fluid passage section. Furthermore, the first conduit 71 and the second conduit 72 have constant fluid passage sections along them.

The coating substance may be supplied to the supply pump 70 selectively and in a controlled manner from the first storage tank 40 through the first conduit 71 or from the second storage tank 50 through the second conduit 72.

The first outlet valve 64 and the second outlet valve 65 may be controlled to allow the coating substance to be supplied alternately from the first storage tank 40 or from the second storage tank 50.

The apparatus 1 comprises at least one delivery nozzle 80 configured to deliver the coating substance and placed in fluid communication with supply assembly 20.

The second fluid circuit 60 comprises a third conduit 81 extended from the supply pump 70, in particular from a delivery head of the supply pump 70, to the delivery nozzle 80 to put the supply pump 70 in fluid communication with the delivery nozzle 80. The second fluid circuit 60 further comprises a third end 82 at which the second fluid circuit 60 is connected to the delivery nozzle 80 and through which the coating substance is supplied to the delivery nozzle 80.

The third conduit 81 is preferably made of stainless steel or of a temperature-resistant plastic material, e.g., PTFE or FEP.

A plurality of third heating elements 90 are associated with the second fluid circuit 60 to heat the coating substance flowing therein. One of the third heating elements 90 is schematically shown in FIG. 4.

In the preferred embodiment, the third heating elements are integrated in respective insulation jackets 91 made of a thermally insulating material and removably fitted on respective portions of the second fluid circuit 60.

The third heating elements 90 may comprise, for example, electrical resistors or heating conduits in which heating fluid circulates.

Figure 4:
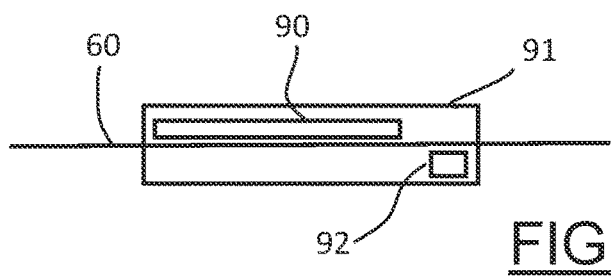
FIG. 4 shows a schematic view of a third detail of the apparatus of FIG. 1.

As shown in FIG. 4, each insulation jacket 91 further comprises a temperature sensor 92 configured to measure the temperature of the portion of the second fluid circuit 60 on which the respective third heating element 90 acts.

In the embodiment shown in FIG. 1, a first insulation jacket 91*a* of the plurality of insulation jackets 91 and the relative heating element 90 are applied on a section of the first conduit 71 extended from the first end 61 to the second junction 73, a second insulation jacket 91*b* of the plurality of insulation jackets 91 and the relative third heating element 90 are applied on a section of the second conduit 72 extended from the second end 62 to the second junction 73, a third insulation jacket 91*d* of the plurality of insulation jackets 91 and the relative third heating element 90 are applied on the common section of the first conduit 71 and the second conduit 72 extended from the second junction 73 to the supply pump 70, and a fourth insulation jacket 91*c* of the plurality of insulation jackets 91 and the relative third heating element 90 are applied on the third conduit 81 extended from the supply pump 70 to the delivery nozzle 80.

In preferred embodiments thereof, the apparatus 1 comprises a plurality of delivery nozzles 80 and a corresponding plurality of third conduits 81, each comprising a respective fourth insulation jacket 91*c* and a respective third heating element 90.

Each delivery nozzle 80 is configured to spray the coating substance onto a respective injection medical device.

Each delivery nozzle 80 can be provided with a respective heating element 85 configured to heat the delivered coating substance. For example, such a heating element can be an electrical resistor applied to the delivery nozzle 80 or incorporated in the delivery nozzle 80.

Each delivery nozzle 80 is configured to nebulise the coating substance by supplying pressurised gas coming from a source 100 of a suitable delivery gas, e.g., compressed air. The source 100 is configured to deliver gas at a pressure comprised between 5 psi (0.34 bar) and 150 psi (10.34 bar), more preferably, about 30 psi (2.07 bar).

The source 100 is associated with each delivery nozzle 80 by a respective conduit 101.

The apparatus 1 comprises a movable support frame configured to support a plurality of injection medical devices, in particular cylinders of respective syringes.

The delivery nozzles 80 and the syringe cylinder support frame are movable with respect to each other to insert/remove each delivery nozzle 80 in a respective cylinder.

In a preferred embodiment, the relative movement between the delivery nozzles 80 and the cylinder support frame is carried out by moving the latter with respect to the delivery nozzles 80, which are fixed.

The first storage tank 40 can be configured in a filling condition in which it receives and stores the coating substance withdrawn from the inlet tank 10. In the filling condition the inlet valve 43 is open towards the second conduit branch 32*a* and closed towards the third conduit branch 32*b*.

The first storage tank 40 can also be configured in a depressurisation condition in which the coating substance that is present therein is depressurised to remove any bubbles. In the depressurisation condition the inlet valve 43 is closed towards the second conduit branch 32*a*, the first outlet valve 64 is closed and the first depressurisation member 45 is activated.

The first storage tank 40 can also be configured in a heating condition in which the coating substance that is present therein is heated. In the heating condition the inlet valve 43 is closed towards the second conduit branch 32*a*, the first outlet valve 64 is closed and the first heating element 47 is activated.

The first storage tank 40 can also be configured in a supply condition in which the coating substance that is present therein is withdrawn to be supplied to the delivery nozzle 80. In the supply condition the inlet valve 43 is closed towards the second conduit branch 32*a*, the first outlet valve 64 is open and the first pressurisation element 44 is activated.

Similarly, the second storage tank 50 can be configured in a filling condition in which it receives and stores the coating substance withdrawn from the inlet tank 10. In the filling condition the inlet valve 43 is open towards the third conduit branch 32*b* and closed towards the first conduit branch 32*a*.

The second storage tank 50 can also be configured in a depressurisation condition in which the coating substance stored therein is depressurised to remove any bubbles. In the depressurisation condition the inlet valve 43 is closed towards the third conduit branch 32*b*, the second outlet valve 65 is closed and the second depressurisation member 55 is activated.

The second storage tank 50 can also be configured in a heating condition in which the coating substance stored therein is heated. In the heating condition the inlet valve 43 is closed towards the third conduit branch 32*b*, the second outlet valve 65 is closed and the second heating element 57 is activated.

The second storage tank 50 can also be configured in a supply condition in which the coating substance stored therein is withdrawn to be supplied to the delivery nozzle 80. In the supply condition the inlet valve 43 is closed towards the third conduit branch 32*b*, the second outlet valve 65 is open and the second pressurisation member 54 is activated.

The apparatus 1 further comprises a control unit 5 operatively connected to at least the inlet valve 43, the first outlet valve 64, the second outlet valve 65, the first pressurisation member 44, the first depressurisation member 45, the first heating element 47, the second pressurisation member 54, the second depressurisation member 55 and the second heating element 57.

The control unit 5 is configured to alternately set the first storage tank 40 and the second storage tank 50 to the supply condition and to alternately maintain, after an initial transient, the first storage tank 40 or the second storage tank 50 in the aforementioned supply condition.

When one between the first storage tank 40 and the second storage tank 50 is in the supply condition, the control unit 5 configures the other between the first storage tank 40 and the second storage tank 50 in the filling condition, then in the depressurisation condition, then in the heating condition. In particular, the control unit 5 is configured to maintain the depressurisation condition for a time comprised between 5 and 30 minutes.

To coat an injection medical device with the coating substance, the coating substance is fed into the inlet tank 10. Preferably, the coating substance comprises a silicone-based oil. Preferably, the injected coating substance has a viscosity greater than 10000 cSt, comprised between 11000 cSt and 14000 cSt, even more preferably comprised between 12000 cSt and 13000 cSt, e.g., about 12500 cSt. Preferably, the coating substance is not pre-sterilised. Preferably, the coating substance and the inlet tank are at room temperature.

Subsequently, the coating substance is withdrawn from the inlet tank 10 pressurising the coating substance in the inlet tank 10 by the service member 21. The coating substance thus exits from the inlet tank 10 and flows into the first conduit branch 31 and, through the first junction 33 and the inlet valve 43, into the second conduit branch 32*a*. In such a case, the inlet valve 43 is open towards the second conduit branch 32*a* and closed towards the third conduit branch 32*b*.

Next, the coating substance is filtered by the first sterilisation filter 30*a* and fed into the first storage tank 40 through the second conduit 41.

In this way, the coating substance is stored in the first storage tank 40.

Subsequently, the second conduit branch 32*a* is closed by the inlet valve 43 to isolate the coating substance stored in the first storage tank 40.

Next, the coating substance stored in the first storage tank 40 is depressurised. Such depressurisation is performed by the first depressurisation member 45. The pressure of the coating substance in the first storage tank 40 is brought to a value less than the atmospheric pressure, preferably comprised between 50 mbar and 400 mbar, even more preferably comprised between 100 mbar and 300 mbar, e.g., about 200 mbar, for a time comprised between 5 and 30 minutes, in order to remove any bubbles.

After having depressurised the coating substance stored in the first storage tank 40, such coating substance is heated by the first heating element 47. In particular, the coating substance is heated until reaching a temperature of 100° C. or higher, preferably 120° C. Alternatively, the coating substance may be heated before or during the depressurisation in the first storage tank 40.

After having entered the coating substance into the first storage tank 40, the inlet valve 43 closes the second conduit branch 32*a* and opens the third conduit branch 32*b*. Thereby, the coating substance may be fed from the inlet tank 10 to the second storage tank 50 through the second sterilisation filter 30*b*.

The coating substance is thus stored in the second storage tank 50.

Next, the third conduit branch 32*b* is closed by the inlet valve 43 to isolate the coating substance stored in the second storage tank 50.

Next, the coating substance stored in the second storage tank 50 is depressurised. Such depressurisation is performed by the second depressurisation member 55. The pressure of the coating substance in the second storage tank 50 is brought to a value less than the atmospheric pressure, preferably comprised between 50 mbar and 400 mbar, even more preferably comprised between 100 mbar and 300 mbar, e.g., about 200 mbar, for a time comprised between 5 and 30 minutes, in order to remove any bubbles.

After having depressurised the coating substance stored in the second storage tank 50, such coating substance is heated by the second heating element 57. In particular, the coating substance is heated until reaching a temperature of 100° C. or higher, preferably 120° C. Alternatively, the coating substance may be heated before or during the depressurisation in the second storage tank 50.

Subsequently, the coating substance is supplied to the delivery nozzle 80 from the first storage tank 40 by operating the supply pump 70, opening the first outlet valve 64 while keeping the second outlet valve 65 closed and pressurising the coating substance in the first storage tank 40 by the first pressurisation member 44. The pressure of the coating substance in the first storage tank 40 is raised to a value greater than the atmospheric pressure and less than 2.5 bar, preferably less than 2 bar.

The coating substance thus flows out of the first storage tank 40, through the first conduit 71, the supply pump 70 and the third conduit 81 until it reaches the delivery nozzle 80.

While the coating substance is supplied to the delivery nozzle 80 from the first storage tank 40 the coating substance is further heated, in particular by the third heating elements 90.

While the coating substance is supplied to the delivery nozzle 80 from the first storage tank 40, further coating substance coming from the inlet tank 10 is fed, stored, depressurised and heated in the second storage tank 50, in accordance with the above.

When the coating substance in the first storage tank 40 is over or below a predetermined minimum level, the supply of coating substance to the delivery nozzle 80 from the first storage tank 40 is interrupted, in particular by closing the first outlet valve 64. Next, the coating substance is supplied to the delivery nozzle 80 from the second storage tank 50. Thereby, there is no interruption in the supply of coating substance to the delivery nozzle 80.

In order to supply the coating substance to the delivery nozzle 80 from the second storage tank 50, the second outlet valve 65 is opened while keeping the first outlet valve 64 closed, the coating substance is pressurised in the second storage tank 50, in particular by the second pressurisation member 54. The pressure of the coating substance in the second storage tank 50 is raised to a value greater than the atmospheric pressure and less than 2.5 bar, preferably less than 2 bar.

The coating substance thus flows out of the second storage tank 50, through the second conduit 72, the supply pump 70 and the third conduit 81 until it reaches the delivery nozzle 80.

While the coating substance is supplied to the delivery nozzle 80 from the second storage tank 50 the coating substance is further heated, in particular by the third heating elements 90.

While the coating substance is supplied to the delivery nozzle 80 from the second storage tank 50, further coating substance from the inlet tank 10 is fed, stored, depressurised and heated in the first storage tank 40, in accordance with the above.

When the coating substance in the second storage tank 50 is over or below a predetermined minimum level, the supply of coating substance to the delivery nozzle 80 from the second storage tank 50 is interrupted, in particular by closing the second outlet valve 65. Subsequently, the cycle is restarted by supplying the coating substance to the delivery nozzle 80 from the first storage tank 40.

The coating substance supplied to the delivery nozzle 80 is nebulised in the delivery nozzle 80 by supplying pressurised gas from the source 100.

The nebulised coating substance is then delivered from the delivery nozzle 80 onto an injection medical device so as to obtain on the latter an average thickness, measured by optical reflectometry, comprised between 100 and 200 nm and with a thickness standard deviation of 50 nm or less, preferably 40 nm or less, more preferably 30 nm or less and even more preferably 20 nm or less.

The preferred embodiments of the disclosure have been described above to explain the principles of the present disclosure and its practical application to thereby enable others skilled in the art to utilize the present disclosure. However, as various modifications could be made in the constructions and methods herein described and illustrated without departing from the scope of the present disclosure, it is intended that all matter contained in the foregoing description or shown in the accompanying drawings, including all materials expressly incorporated by reference herein, shall be interpreted as illustrative rather than limiting. Thus, the breadth and scope of the present disclosure should not be limited by the above-described exemplary embodiment but should be defined only in accordance with the following claims appended hereto and their equivalents.

What is claimed is:

1. An apparatus for coating an injection medical device, comprising:
   an inlet tank fillable with a coating substance;
   a delivery nozzle;
   a supply assembly interposed between, and in fluid communication with, said inlet tank and said delivery nozzle, said supply assembly being configured to withdraw the coating substance from said inlet tank and to supply it to said delivery nozzle; and
   characterized in that said delivery nozzle is configured to deliver said coating substance to an injection medical device and in that said supply assembly comprises at least one sterilisation filter configured to filter the coating substance withdrawn from said inlet tank.

2. The apparatus of claim 1, wherein said supply assembly further comprises a first storage tank interposed between, and in fluid communication with, a first sterilisation filter and said delivery nozzle, wherein said first storage tank is configured to receive and temporarily store the coating substance withdrawn from said inlet tank and intended to be supplied to the delivery nozzle; and
   wherein said first storage tank is selectively configurable in:
      a filling condition wherein said first storage tank receives and stores the coating substance withdrawn from the inlet tank; and
      a supply condition wherein the coating substance stored in the first storage tank is withdrawn from the first storage tank to be supplied to the delivery nozzle.

3. The apparatus of claim 2, wherein said supply assembly further comprises a second storage tank interposed between, and in fluid communication with, a second sterilisation filter and said delivery nozzle, wherein said second storage tank is configured to receive and temporarily store the coating substance withdrawn from said inlet tank and intended to be supplied to the delivery nozzles; and
   wherein said second storage tank is selectively configurable in:
      a filling condition wherein said second storage tank receives and stores the coating substance withdrawn from the inlet tank; and
      a supply condition wherein the coating substance stored in the second storage tank is withdrawn from the second storage tank to be supplied to the delivery nozzle.

4. The apparatus of claim 2, wherein said supply assembly further comprises:
   a second storage tank interposed between, and in fluid communication with, a second sterilisation filter and said delivery nozzle, wherein said second storage tank is configured to receive and temporarily store the coating substance withdrawn from said inlet tank and intended to be supplied to the delivery nozzle;
   at least one first heating element configured to heat the coating substance stored in said first storage tank;
   at least one second heating element configured to heat the coating substance stored in said second storage tank.

5. The apparatus of claim 4, wherein:
   said at least one first heating element is arranged inside a first insulating jacket placed outside the first storage tank and in which one or more electrical resistors are positioned or in which a heating fluid circulates;
   said at least one second heating element is arranged inside a second insulating jacket placed outside the second storage tank and in which one or more electrical resistors are positioned or in which a heating fluid circulates.

6. The apparatus of claim 5, wherein the first storage tank is removable from the first insulating jacket and the second storage tank is removable from the second insulating jacket.

7. The apparatus of claim 2, further comprising:
   a second storage tank interposed between, and in fluid communication with, a second sterilisation filter and said delivery nozzle, wherein said second storage tank is configured to receive and temporarily store the coating substance withdrawn from said inlet tank and intended to be supplied to the delivery nozzle;
   wherein said second storage tank is selectively configurable in a filling condition wherein said second storage tank receives and stores the coating substance withdrawn from the inlet tank; and a supply condition wherein the coating substance stored in the second storage tank is withdrawn from the second storage tank to be supplied to the delivery nozzle;
   the apparatus further comprising a control unit operatively connected with said first storage tank and said second storage tank, wherein said control unit is configured to:
   set in said first storage tank said supply condition when said second storage tank is in said filling condition, and
   set in said second storage tank said supply condition when said first storage tank is in said filling condition.

8. The apparatus of claim 3,
   wherein said supply assembly further comprises:
      a first fluid circuit having a first end coupled to said inlet tank, a second end coupled to said first storage tank and a third end coupled to said second storage tank; and
      a second fluid circuit having a first end coupled to said first storage tank, a second end coupled to said second storage tank and a third end coupled to said delivery nozzle.

9. The apparatus of claim 8, said supply assembly further comprising at least one insulation jacket removably placed around at least part of said second fluid circuit.

10. The apparatus of claim 9, said supply assembly further comprising at least one third heating element arranged inside said at least one insulation jacket.

* * * * *